(12) United States Patent
Chabane et al.

(10) Patent No.: US 11,904,156 B2
(45) Date of Patent: Feb. 20, 2024

(54) SYSTEM FOR GENERATING A BLOOD CIRCULATION

(71) Applicant: Procope Medicals, Nantes (FR)

(72) Inventors: Saïd Chabane, Nantes (FR); Samuel Plumejault, Angers (FR)

(73) Assignee: PROCOPE MEDICALS, Nantes (FR)

( * ) Notice: Subject to any disclaimer, the term of this patent is extended or adjusted under 35 U.S.C. 154(b) by 607 days.

(21) Appl. No.: 17/273,550

(22) PCT Filed: Aug. 20, 2019

(86) PCT No.: PCT/EP2019/072277
§ 371 (c)(1),
(2) Date: Mar. 4, 2021

(87) PCT Pub. No.: WO2020/048768
PCT Pub. Date: Mar. 12, 2020

(65) Prior Publication Data
US 2021/0339000 A1    Nov. 4, 2021

(30) Foreign Application Priority Data

Sep. 5, 2018  (FR) ...................................... 1857952

(51) Int. Cl.
*A61M 60/435* (2021.01)
*A61M 60/538* (2021.01)
(Continued)

(52) U.S. Cl.
CPC ........ *A61M 60/435* (2021.01); *A61M 1/3627* (2013.01); *A61M 60/148* (2021.01);
(Continued)

(58) Field of Classification Search
CPC .............. A61M 60/268; A61M 60/435; A61M 60/538; A61M 1/3627; A61M 60/148; A61M 60/876; A61M 60/196
See application file for complete search history.

(56) References Cited

U.S. PATENT DOCUMENTS 3,597,766 A    8/1971  Buck
3,755,825 A    9/1973  DeBakey et al.
(Continued)

FOREIGN PATENT DOCUMENTS

| | | |
|---|---|---|
| EP | 0467999 A1 | 1/1992 |
| EP | 0467999 B1 | 8/1994 |
| WO | 9108003 A1 | 6/1991 |

OTHER PUBLICATIONS

International Search Report dated Sep. 26, 2019 for corresponding International Application No. PCT/EP2019/072277, Aug. 20, 2019.
(Continued)

*Primary Examiner* — Suba Ganesan
(74) *Attorney, Agent, or Firm* — David D. Brush; Westman, Champlin & Koehler, P.A.

(57) ABSTRACT

A system for generating a blood circulation in at least part of an organ of a vertebrate, including a first artificial cavity and a second artificial cavity. The cavities each include a flexible membrane capable of beating under the action of a gas. Each of the membranes separate in a sealed manner a blood circulation chamber and a chamber containing the gas. The system also includes: a first low pressure gas buffer reservoir; a second high-pressure gas buffer reservoir; a gas distribution; and a pneumatic pump.

10 Claims, 2 Drawing Sheets

(51) Int. Cl.
*A61M 60/148* (2021.01)
*A61M 60/876* (2021.01)
*A61M 1/36* (2006.01)
*A61M 60/268* (2021.01)

(52) U.S. Cl.
CPC ........ *A61M 60/268* (2021.01); *A61M 60/538* (2021.01); *A61M 60/876* (2021.01); *A61M 2205/0266* (2013.01); *A61M 2205/0294* (2013.01)

(56) References Cited

U.S. PATENT DOCUMENTS

| | | |
|---|---|---|
| 4,516,567 A | 5/1985 | Veragen |
| 5,232,434 A * | 8/1993 | Inagaki ............... A61M 60/538 623/3.28 |
| 5,269,811 A | 12/1993 | Hayes et al. |

OTHER PUBLICATIONS

Written Opinion of the International Searching Authority dated Sep. 26, 2019 for corresponding International Application No. PCT/EP2019/072277, filed Aug. 20, 2019.
English translation of the Written Opinion of the International Searching Authority dated Oct. 8, 2019 for corresponding International Application No. PCT/EP2019/072277, filed Aug. 20, 2019.

* cited by examiner

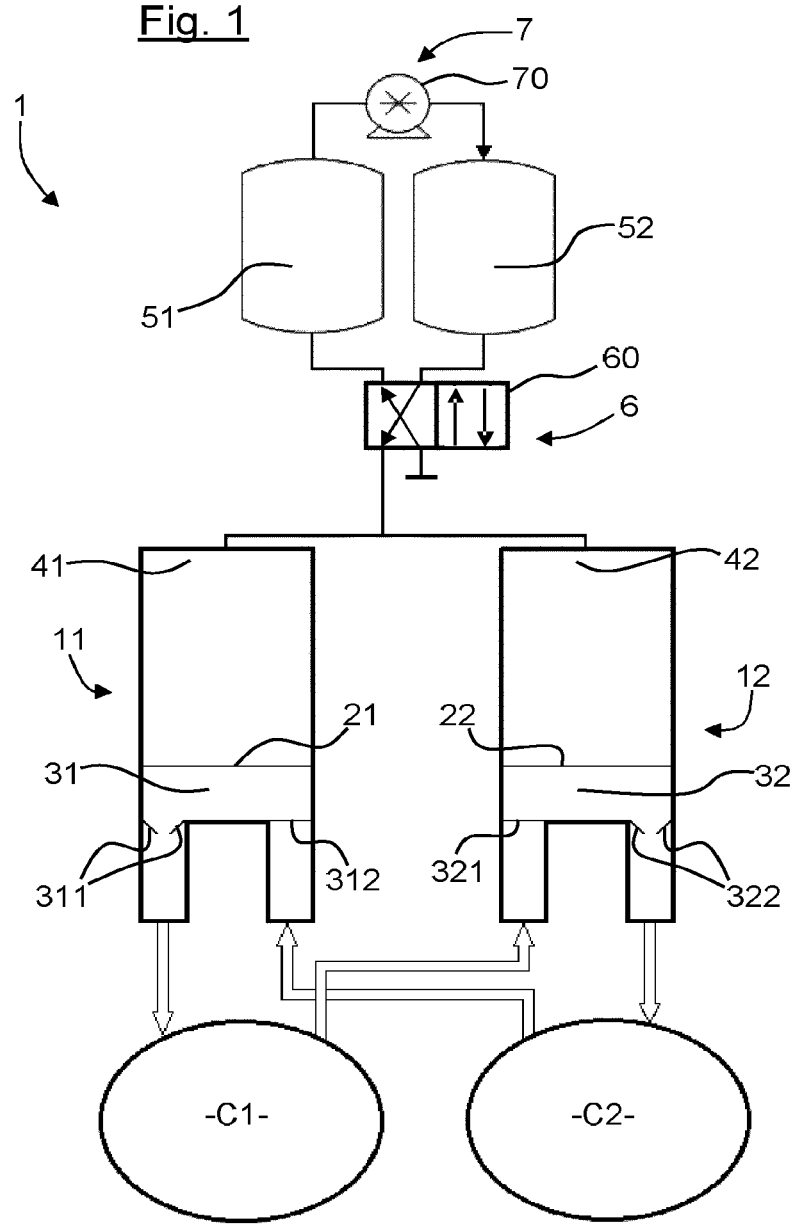

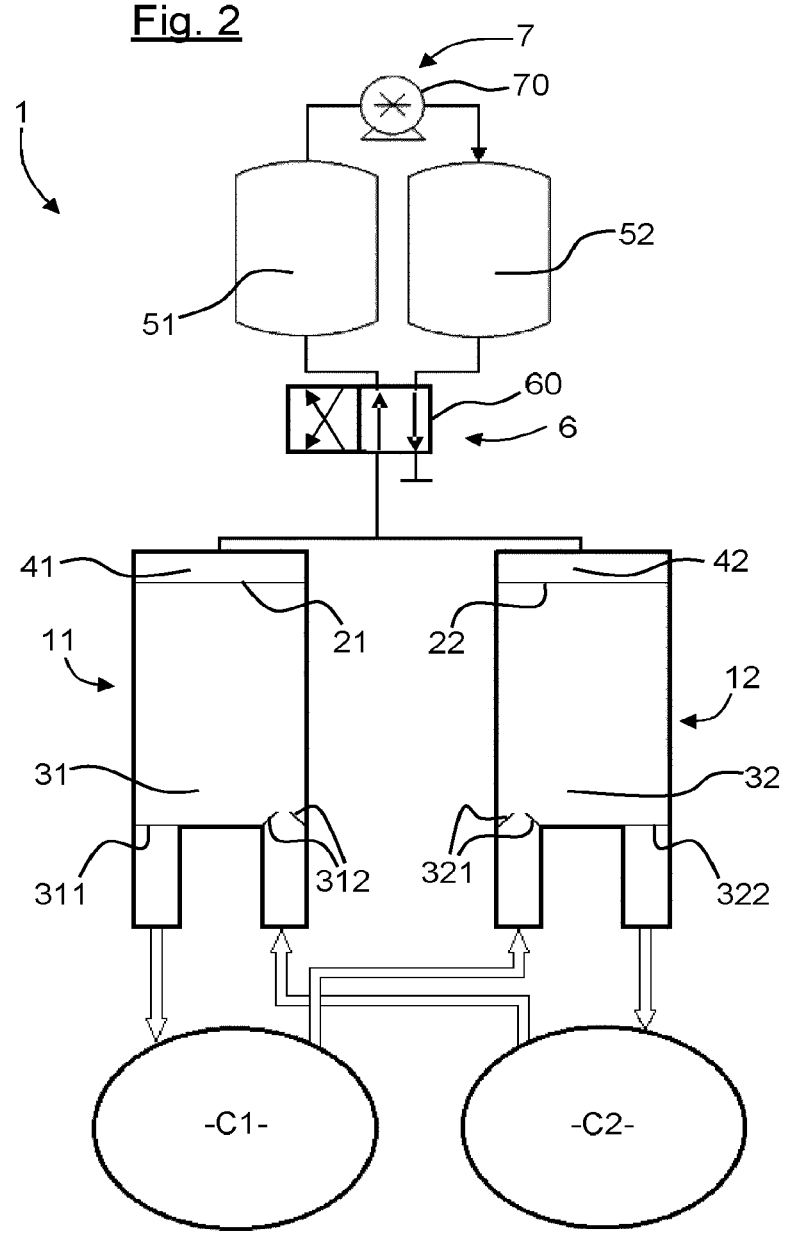

SYSTEM FOR GENERATING A BLOOD CIRCULATION

CROSS-REFERENCE TO RELATED APPLICATIONS

This Application is a Section 371 National Stage Application of International Application No. PCT/EP2019/072277, filed Aug. 20, 2019, the content of which is incorporated herein by reference in its entirety, and published as WO 2020/048768 on Mar. 12, 2020, not in English.

FIELD OF THE DISCLOSURE

The field of invention is that of the design and manufacture of medical devices and equipment.

More precisely, the invention concerns equipment for artificially creating a blood flow that is classically provided by the heart of a vertebrate. The invention relates in particular but not exclusively to medical equipment implantable in the pericardial cavity of a vertebrate.

BACKGROUND OF THE DISCLOSURE

In the field of invention, we know the equipment implementing the pneumatic pump concept and those implementing the hydraulic pump concept.

Historically, the first artificial cores have used the concept of pneumatic pumps. These artificial hearts have to be implanted inside a patient's rib cage, and external equipment, capable of generating air pressure, is connected to the artificial heart to activate it by means of an air flow.

In this technology, the artificial heart comprises artificial cavities inside which flexible membranes are located. Within a cavity, a membrane then separates a blood circulation chamber and a gas chamber in a sealed manner. Via connecting hoses that connect the external equipment to the artificial heart, pulsed compressed air is supplied to the gas chamber in each of the artificial cavities to generate blood flow using the membrane pump principle.

This type of solution is robust and reliable.

However, this concept requires particularly heavy external equipment and involves the introduction of air ducts inside the body to the artificial heart. Thus, the patient equipped with this artificial heart does not enjoy a significant autonomy.

In the second type of technology, an artificial heart with a hydraulic motor system was proposed.

This hydraulic core has an anthropomorphic design and makes it possible to gain significant autonomy compared to the artificial cores previously described, using pneumatic technology.

Indeed, this type of hydraulic artificial heart, based on the idea of the diaphragm pump, incorporates the motor system that generates pulsatile pressure directly inside the artificial heart.

Such an artificial heart uses a temporary battery implanted inside the vertebrate's body, and requires only an external battery recharging system that does not involve any invasive connectors designed to enter the body to electrically power the heart.

However, such a system is less robust and reliable than hearts using pneumatic technology.

The solution described in the patent document published under number U.S. Pat. No. 4,516,567, which discloses a total pneumatic artificial heart operating with a single pump, is still known. The pump injects or sucks air at the membranes to generate blood flow.

The disadvantage of such a heart is that it requires a high-performance pump that can be heavily stressed during each sub-period of a cardiac operating cycle, as the pump directly injects/aspires the volume of fluid displaced to or from the membranes.

SUMMARY

One of the objectives of the invention is to resolve these drawbacks of the state of the art.

One of the objectives of the invention is to propose a system for generating a blood circulation that is more robust and reliable than the solutions of the prior art implementing the concept of the hydraulic heart.

The invention also aims to provide such an energy-efficient blood circulation generating system.

The invention also aims to provide such a system which is less cumbersome than the solutions according to prior art which implement the pneumatic pump concept.

More specifically, the invention is intended to provide such a solution which is so small that it can easily be implemented inside a total artificial heart intended to be implanted in the rib cage of a vertebrate.

These objectives, as well as others which will appear subsequently, are achieved by the invention which has as its object a system for generating a blood circulation in at least part of an organ of a vertebrate, comprising a first artificial cavity and a second artificial cavity, said cavities each comprising a flexible membrane capable of beating under the action of a gas, each of said membranes sealingly separating a blood circulation chamber and a chamber containing said gas, characterised in that it comprises:

a first gas buffer reservoir intended to be brought substantially to a first pressure, so-called low pressure, and a second gas buffer reservoir intended to be brought substantially to a second pressure higher than said first pressure, so-called high pressure;

gas distribution means connected to the chambers containing said gas of said first and second artificial cavities and to said first and second buffer reservoirs, arranged to alternately inject gas into said chambers containing said gas and expel gas from said chambers containing said gas to provide predetermined values of blood flow rates in the blood flow chambers of said first cavity and said second cavity;

a pneumatic pump supplied with electrical energy mounted between said first buffer reservoir and said second buffer reservoir and intended to suck gas from said first tank to inject it into said second tank.

Thanks to the generation system according to the invention, blood circulation can be artificially generated without the system being as cumbersome as pneumatic systems according to the anterior art using external equipment. The generation system according to the invention may also have a much lower energy consumption than pneumatic systems according to the prior art.

Indeed, according to the principle of the invention, the pneumatic pump's only role is to maintain a pressure difference between the first gas buffer reservoir and the second gas buffer reservoir.

This pump, unlike the previous art, is not intended to directly inject and suck the motive fluid (here the gas) at the level of the chambers containing said gas in each artificial cavity.

According to the invention, the first gas buffer reservoir and the second gas buffer reservoir are used to supply or withdraw motive fluid from the chambers containing said gas to make the flexible membranes beat and create blood circulation.

As a result, the use of a single pump to generate a pressure difference between the first gas buffer reservoir and the second gas buffer reservoir allows the system to have a low overall energy consumption, and in particular lower than that of pneumatic systems according to the previous art.

In other words, the first gas buffer reservoir and the second gas buffer reservoir serve as an energy storage reserve. The distribution of this energy is permitted and controlled by gas distribution means which connect the chambers containing said gas to the first gas buffer reservoir and the second gas buffer reservoir.

Preferably, said first and second artificial cavities, said first and second gas buffer reservoirs, said gas distribution means and said pneumatic pump form an integral unit and the system for generating a blood circulation further comprises a battery for supplying electrical power to said pump and said gas distribution means.

In this way, the generation system according to the invention can, at least temporarily, be self-sufficient and has an advantageous autonomy to supply blood to the organ(s) connected to the system.

A preferred characteristic of this pump is that it is a vane pump.

The rotary vane pump, used to generate a high pressure in the second gas buffer reservoir and a lower pressure in the first gas buffer reservoir, is particularly suitable to enable the generation system according to the invention to have a low overall energy consumption.

This vane pump compensates for internal leakage and flow rates consumed by the heart pump drive.

As a further advantageous feature, said gas distribution means comprise at least one piezoelectric switch and/or at least one shape memory switch and/or at least one electromagnetic switch.

Such means of gas distribution form particularly suitable solutions for miniaturising these means of distribution.

Preferably, said gas is air.

Such a gas allows the system to operate normally and simply without the need for a specific gas supply that would be expensive and potentially difficult to obtain.

It should be noted that the values of the first and second pressure are adjusted according to the patient.

The pressure in the buffer reservoirs is regulated according to the heartbeat to ensure a blood flow corresponding to the patient's needs.

This control is done electronically via sensors integrated in the system.

Advantageously, said gas distribution means comprise a 4-way, 2-position valve.

These gas distribution means ensure gas exchanges between the first gas buffer reservoir and the second gas buffer reservoir with the chambers containing said gas of the artificial cavities.

In this case, the valve is preferably a pilot-operated flap valve and/or a pilot operated slide valve.

A first preferred solution is that the system for generating a blood circulation forms a total cardiac prosthesis to be implanted in a patient's pericardial cavity and capable of replacing the patient's left and right ventricles after their removal, with the first and second cavity forming a biventricular module, the blood circulation chamber of the first artificial cavity being intended to be connected to the left atrium and the aorta of said patient and the blood circulation chamber of the second artificial cavity being intended to be connected to the right atrium and the pulmonary artery of said patient.

Such a total cardiac prosthesis then makes it possible to combine the robustness and reliability of pneumatic implants with the small dimensions of total prostheses using a hydraulic motor fluid according to the anterior art. Moreover, the total cardiac prosthesis of the total generation system according to the invention can be completely autonomous and require only a small amount of electricity to operate gas distribution means and the pneumatic pump.

According to a second preferential solution, the system for generating a blood circulation forms a circuit for the ex-vivo perfusion of said organ, making it possible to keep said organ alive for a transplant.

Indeed, the generation system according to the invention then makes it possible to ensure extracorporeal blood circulation thanks to an apparatus which is particularly compact, which is less bulky than those known in the anterior art, and which requires only a very low energy input (of the order of 15 W to 20 W).

Preferably, a system for generating a blood circulation such as those described above comprises one and only one pneumatic pump.

BRIEF DESCRIPTION OF THE DRAWINGS

Other characteristics and advantages of the invention will become clearer on reading the following description of a preferred mode of making the invention, given as an illustrative and non-limitative example, and the appended drawings among which:

FIG. 1 is a schematic representation of the system for generating a blood circulation according to the invention, in which the chambers containing said gas are connected to the second (high-pressure) gas buffer reservoir, the blood circulation chambers then having a small volume;

FIG. 2 is a schematic representation of the same system for generating a blood circulation, in which the chambers containing said gas are connected to the first (low-pressure) gas buffer reservoir, the blood circulation chambers then having a large volume.

DETAILED DESCRIPTION OF ILLUSTRATIVE EMBODIMENTS

With reference to FIGS. 1 and 2, the system for generating a blood circulation 1 allows the artificial generation of blood flow in at least one part of a vertebrate organ. Specifically, System 1 is used to generate blood flow in two circuits of a blood stream, including:

a first circulation circuit of the blood flow C1;

a second circulation circuit of the C2 blood flow.

As will be detailed later, System 1 for generating blood circulation can form a total heart prosthesis as a first preferred solution. In this case, for example, the first circulation circuit of blood flow C1 corresponds to an anatomical circulation circuit supplying the body of a vertebrate with oxygenated blood, and the second circulation circuit of blood flow C2 corresponds to another anatomical circulation circuit intended to oxygenate the blood (this other circulation circuit integrating notably the lungs of the vertebrate).

According to a second preferred solution, the system for generating a blood circulation 1 can form an ex-vivo blood circulation circuit of an organ. In this case, at least one of the first circulation circuit of blood flow C1 or the second circulation circuit of blood flow C2 is then coupled to the organ to supply it with blood.

As shown in FIGS. 1 and 2, System 1 for generating a blood circulation includes:
- a first artificial cavity 11;
- a second artificial cavity 12;
- a first gas buffer tank 51;
- a second gas buffer tank 52;
- gas distribution means 6 coupling the first artificial cavity 11 and the second artificial cavity 12 to the first gas buffer tank 51 and the second gas buffer tank 52;
- a pneumatic pump 7 coupled to the first gas buffer tank 51 and the second gas buffer tank 52.

The first artificial cavity 11 and the second artificial cavity 12 each comprise a flexible membrane 21, 22 that can be beaten by the action of a gas. Indeed, the system for generating a blood circulation 1 is a pneumatic system and uses a gas as the driving fluid to allow the generation of blood circulation. This gas is preferably air.

These flexible membranes 21, 22 are elastic and divide, respectively, the first artificial cavity 11 and the second artificial cavity 12 into two chambers.

More specifically:
- the flexible membrane 21 of the first artificial cavity 11 separates in a sealed manner, within this first cavity 11, a blood circulation chamber 31 and a chamber containing said gas 41;
- the flexible membrane 22 of the second artificial cavity 12 separates in a sealed manner, within this second cavity 12, a blood circulation chamber 32 and a chamber containing said gas 42.

The first artificial cavity 11 and the second artificial cavity 12 also comprise:
- injection valves 312, 321 of blood in the blood circulation chambers 31, 32;
- ejection valves 311, 322 of blood from the blood circulation chambers 31, 32.

These injection valves 312, 321 and ejection valves 311, 322 ensure that the direction of blood flow in the system is guaranteed. Specific settings for each 311, 312, 321, 322 valve enable the operating pressures of the artificial cavities to be adjusted.

As previously explained, the flexible membranes 21, 22 are able to beat under the action of gas.

The flexible membranes 21, 22 each vary the volume of the blood circulation chambers 31, 32 by beating.

When the volume of a blood circulation chamber 31, 32 is increased, the pressure in the blood circulation chamber 31, 32 drops and causes the ejection valves 311, 322 to close and the injection valves 312, 321 to open, allowing the blood circulation chamber 31, 32 to be filled with blood.

On the contrary, when the volume of a blood circulation chamber 31, 32 is reduced, the pressure within the blood circulation chamber 31, 32 increases and causes the injection valves 312, 321 to close and the ejection valves 311, 322 to open, allowing the blood to be expelled from the blood circulation chamber.

The gas exchanges (injection and extraction) at the level of the chambers containing said gas 41, 42 are ensured by:
- gad distribution means 6;
- the first gas buffer reservoir 51;
- the second gas buffer reservoir 52;
- the pneumatic pump 7.

The first gas buffer tank 51 is intended to be raised to a first pressure, the so-called low pressure.

As for the second gas buffer tank 52, it is intended to be raised to a second pressure, called high pressure, the second pressure being higher than the first pressure.

As an example, the first pressure can be increased to 1.1 bar and the second pressure can be increased to 1.15 bar.

Preferably, the operation of the pneumatic pump is dependent on the "heart rate" defined by the means of gas distribution, to keep the pressures within the above limits.

In this case, the control of system 1 is carried out electronically by means of sensors integrated in the system.

As shown in FIGS. 1 and 2, the pneumatic pump 7 is mounted between the first buffer tank 51 and the second buffer tank 52.

The pneumatic pump 7 sucks gas from the first buffer tank 51 and injects it into the second buffer tank 52. In this way, the pneumatic pump 7 allows the first buffer tank 51 to be maintained at approximately its low pressure and the second buffer tank 52 to be maintained at approximately its high pressure.

To operate, this pneumatic pump 7 is supplied with electrical energy.

This pump is advantageously a vane pump 70. The vane pump is a positive displacement transfer pump, consisting of a stator (stationary) and a rotor (mobile) that rotates tangentially to the stator. The vanes are fixed to the rotor and can slide in rotor housings, perpendicularly to the axis of rotation of the rotor, to come into contact with the stator walls by centrifugal force. In addition to the centrifugal force, the rotor may possibly include means for returning the vanes to a position in contact with the stator walls.

Preferably and as shown in the figures, the pneumatic pump 7 is unique.

As explained above, gas distribution means 6 are coupled to the first artificial cavity 11, the second artificial cavity 12 and the buffer tanks. Specifically, gas distribution means 6 are connected to the gas chambers 41, 42, the first buffer tank 41, and the second buffer tank 42.

Gas distribution means 6 are arranged to alternately inject gas into and extract gas from the chambers containing said gas 41, 42, to ensure predetermined values of blood flow rates in the blood circulation chambers of the artificial cavities.

In other words, gas distribution means 6 (as well as the buffer tanks) allow the pressure of the chambers containing said gas 41, 42 to be modified in such a way as to cause an expansion or reduction in the volume of these chambers thanks to the elastic deformation of the flexible membranes 21, 22.

A repetitive variation in the volume of the chambers containing said gas mechanically leads to a repetitive variation in the volume of the blood circulation chambers 31, 32.

This variation in the volume of the blood circulation chambers 31, 32 also results in a variation in the blood pressure within these chambers.

Therefore, gas distribution means 6, by alternately injecting and extracting gas, creates a blood flow by pumping blood into the blood circulation chambers 31, 32 and expelling the blood from these blood circulation chambers 31, 32 by means of the injection valves 312, 321 and the ejection valves 311, 322 described above.

Preferably, gas distribution means 6 comprise at least one piezoelectric switch and/or at least one shape memory switch and/or at least one electromagnetic switch.

As shown in FIGS. 1 and 2, the means of gas distribution 6 includes a 4-way, 2-position 60 valve. The valve 60 can be a pilot operated spool valve 60 or a flap valve.

In fact, with reference to FIG. 1, the distributor 60 adopts a first position in which the second buffer tank 52 (high pressure) communicates with the chamber containing said gas 41 of the first artificial cavity 11 and with the chamber containing said gas 42 of the second artificial cavity 12. In this case, the high pressure gas in the second buffer tank 52 is injected into the chambers containing said gas 41, 42.

Following the passage of valve 60 in its second position and as shown in FIG. 2, the second buffer tank 52 no longer communicates with the chambers containing said gas 41, 42, which then communicate with the first buffer tank 51 (low pressure) and the gas.

According to the present embodiment, the chambers containing said gas 41, 42 communicate at the same time with the first buffer tank 51 or with the second buffer tank 52. As a result, the blood circulation chambers 31, 32 fill and expel blood synchronously.

In other possible embodiments, the valve can be configured to desynchronise the filling and expulsion of blood from the blood circulation chambers 31, 32 and/or to carry out these fills or expulsions at a different rate between each artificial cavity.

Preferably, the first 11 and second 12 artificial cavities, the first 51 and second 52 gas buffer tanks, gas distribution means 6 and the pneumatic pump 7 form a one-piece unit.

The system for generating a blood circulation 1 also comprises a battery for supplying electrical energy to the pneumatic pump 7 and gas distribution means 6 for installation in an abdominal cavity. This battery is recharged by transcutaneous induction.

As mentioned above, system 1 of blood circulation generation can form a total heart prosthesis. In this case, System 1 is intended to be implanted in a patient's pericardial cavity. System 1 can then be used to replace the patient's ventricles (left and right). The first artificial chamber 11 and the second artificial chamber 12 thus form a biventricular module, with blood flow chamber 31 of the first artificial chamber 11 being connected to the patient's left atrium and aorta, and blood flow chamber 32 of the second artificial chamber 12 being connected to the patient's right atrium and pulmonary artery.

An example of the operating cycle of the total heart prosthesis is developed below.

Systole is the ejection of blood from the blood circulation chambers (artificial ventricles) into the blood circulation circuits C1, C2.

Diastole is the injection of the blood contained in the blood circulation circuits C1, C2 (blood from the left and right atria) into the blood circulation chambers 31, 32 (aspiration of blood into the artificial ventricles).

The change from diastole to systole and vice versa results in a change in the pressure development in the blood flow chambers 31, 32 (increase and decrease in pressure) and results in a change in the state of the injection valves 312, 321 and the ejection valves 311, 322.

During the transition from diastole to systole, the ejection valves 311, 322 (aortic and pulmonary valves) change from closed to open state, and the injection valves 312, 321 (atrioventricular valves) change from open to closed state.

When changing from systole to diastole, the ejection valves 311, 322 (aortic and pulmonary valves) change from open to closed state, and the injection valves 312, 321 (atrioventricular valves) change from closed to open state.

In the initial state of systole, the chambers containing said gas 41, 42 each have a volume of the order of 5 mL with a pressure of the order of 0.107 Bar, the blood circulation chambers 31, 32 (artificial ventricles) are filled with blood, the valve 60 has been switched and the chambers containing said gas 41, 42 have just been connected to the second buffer reservoir 52 (high pressure).

The pressure in the chambers containing said gas 41, 42 increases and causes the deformation of the elastic membranes 21, 22. The pressure in the chambers containing said gas increases in particular up to 0.160 Bar.

The blood circulation chambers 31, 32 are emptied and the blood is sent to the blood circulation circuits C1, C2 (organs and lungs).

In the initial state of diastole, the chambers containing said gas each have a volume of the order of 130 mL with a pressure of the order of 0.160 Bar, the blood circulation chambers 31, 32 (artificial ventricles) are empty of blood (or at their lowest level), the dispenser has been tilted and the chambers containing said gas 41, 42, have just been connected to the first buffer reservoir 51 (low pressure).

The pressure in the chambers containing said gas 41, 42 drops (then returning to 0.107 Bar) and causes the deformation of the elastic membranes 21, 22 leading to an increase in the volume of the blood circulation chambers 31, 32.

The blood circulation chambers 31, 32 (artificial ventricles) fill up.

System 1 according to the invention is configured so that the blood circulation chambers (artificial ventricles) are filled at constant pressure, i.e. on average:
  0.012 Bar for the blood circulation chamber of the first artificial cavity 11 (left artificial ventricle);
  0.005 Bar for the blood circulation chamber of the second artificial cavity 12 (right artificial ventricle).

At the end of the diastole, the systole-diastole cycle can then be restarted.

Although the present disclosure has been described with reference to one or more examples, workers skilled in the art will recognize that changes may be made in form and detail without departing from the scope of the disclosure and/or the appended claims.

The invention claimed is:

1. A system for generating a blood circulation in at least part of an organ of a vertebrate, comprising;
   a first artificial cavity and a second artificial cavity said cavities each comprising a flexible membrane capable of beating under an action of a gas, each of said membranes sealingly separating a blood circulation chamber and a chamber containing said gas
   a first gas buffer reservoir to be brought substantially to a first pressure, referred to as low pressure, and a second gas buffer reservoir to be brought substantially to a second pressure higher than said first pressure, referred to as high pressure;
   a gas distribution connected to the chambers containing said gas of said first and second artificial cavities and to said first and second buffer reservoirs, arranged to alternately inject gas into said chambers containing said gas and expel gas from said chambers containing said gas to provide predetermined values of blood flow rates in the blood circulation chambers of said first cavity and said second cavity; and
   a pneumatic pump supplied with electrical energy and mounted between said first buffer reservoir and said second buffer reservoir and configured to suck gas from said first reservoir in order to inject the gas into said second reservoir.

2. The system for generating a blood circulation according to claim 1, wherein said first and second artificial cavities, said first and second gas buffer reservoirs, said gas distribution and said pneumatic pump form a single-piece assembly and the system further comprises a battery for supplying electrical energy to said pump and said gas distribution.

3. The system for generating a blood circulation according to claim 1, wherein said pump is a vane pump.

4. The system for generating a blood circulation according to claim 1, wherein said gas distribution comprises at least one piezoelectric switch and/or at least one shape memory switch and/or at least one electromagnetic switch.

5. The system for generating a blood circulation according to claim 1, wherein said gas is air.

6. The system for generating a blood circulation according to claim 1, wherein said gas distribution comprises a 4-way, 2-position valve.

7. The system for generating a blood circulation according to claim 6, wherein said valve is a flap valve and/or a pilot operated slide valve.

8. The system for generating a blood circulation according to claim 1, wherein the system forms a total cardiac prosthesis configured to be implanted in the pericardial cavity of a patient and capable of replacing the left and right ventricles of said patient after ablation thereof, the first and second cavity forming a biventricular module, the blood circulation chamber of the first artificial cavity being configured to be connected to the left atrium and the aorta of said patient and the blood circulation chamber of the second artificial cavity being configured to be connected to the right atrium and the pulmonary artery of said patient.

9. The system for generating a blood circulation according to claim 1, wherein the system forms a circuit for ex-vivo perfusion of said organ, making it possible to keep said organ alive for transplantation.

10. The system for generating a blood circulation according to claim 1, wherein the system comprises one and only one pneumatic pump.

* * * * *